US00PP08381P

United States Patent [19]

Klemm

[11] Patent Number: Plant 8,381

[45] **Date of Patent: * Sep. 21, 1993**

[54] GERANIUM PLANT NAMED KLERIFI

[75] Inventor: Siegfried Klemm, Stuttgart, Fed. Rep. of Germany

[73] Assignee: Selecta Klemm, Stuttgart, Fed. Rep. of Germany

[ * ] Notice: The portion of the term of this patent subsequent to Jun. 21, 2008 has been disclaimed.

[21] Appl. No.: 480,092

[22] Filed: Feb. 14, 1990

[51] Int. Cl.[5] ..... A01H 5/00

[52] U.S. Cl. ..... Plt./87.12

[58] Field of Search ..... Plt./68

*Primary Examiner*—James R. Feyrer

[57] ABSTRACT

A new geranium cultivar distinguished by its brilliant cyclamate purple coloring which does not fade under high temperature and high light intensity. This plant blooms continuously from spring to fall, maintaining its color and health permanently. The florets are of medium size and the flowers are well filled with approximately twelve florets in each cluster.

1 Drawing Sheet

BACKGROUND

This new variety of geranium plant originated in 1987 as a sport of the geranium variety "Rigi" in my nursery in Stuttgart, West Germany. The unusual dark color, its growth characteristics and the abundance of flowers caused it to be selected for propagation which was done by me by means of cuttings. Reproduction of successive generations of this plant have shown that its novel and distinguishing characteristics are fixed and hold true from generation to generation.

DESCRIPTION OF THE DRAWING

The new variety of geranium plant is illustrated by the accompanying full color photographic drawing, which shows the red purple coloring and the growth characteristics as true as it is reasonably possible to obtain by conventional photographic procedures.

DESCRIPTION OF THE PLANT

The following is a detailed description of my new geranium variety as observed of plants grown both in the greenhouse and outdoors at Stuttgart, West Germany, with the color designation being according to The R.H.S. Colour Chart published by The Royal Horticultural Society of London, England.

THE PLANT

Origin: Sport.
Parentage: Rigi (unpatented).
Classification:
*Botanic.*—*Pelargonium peltatum.*
*Commercial.*—Ivy geranium.
Form: Normally, a hanging bush, having a shape like ivy.
Growing rate: Medium.
Branching character: Medium.
*Tendrils.*—About 35 cm. long from a hanging plant.
Growth habit:
*Strength.*—Medium.
Foliage:
*Quantity.*—Medium.
*Shape of leaf.*—Like ivy with entire margins.
*Size.*—Small.
*Texture.*—Leathery.

*Color.*—Upper side — Green. Under side — Lighter green.

THE BUD

Size: Small.
*Diameter.*—About 10 mm.
*Length.*—About 12 mm.
Shape: Ovoid and pointed.
Opening rate: Medium.
Colors of petals:
*When sepals first divide.*—Light Purple.
*When petals begin to unfurl.*—Purple Violet.
Sepals:
*Number.*—5.
*Shape.*—Small and pointed.
*Character.*—The sepals stand up when the florets open.
*Color.*—Inside — Light Green. Outside — Green.
Calyx:
*Shape.*—Cup-shaped.
*Aspect.*—Smooth.
*Splitting.*—Calyx does not split.

INFLORESENCE

Blooming habit: Continuous and profuse from early Spring to late Fall.
Size of flower:
*Diameter.*—In average about 4 cm.
Borne: In a cluster on a strong stalk.
Florets:
*Number.*—About 12.
Petalage:
*Number.*—About 9 or 10.
*Form.*—Obovate with entire margins.
*Arrangement.*—Imbricated.
*Persistance.*—Petals stay on stem about 14 days.
*Texture.*—Soft.
*Appearance.*—Satiny.
*Color.*—74A on the body of the petal. 74B at the base portions of the petal. 58A on small stripes on the reverse side of two petals.
Flower Stem:
*Length.*—About 12 cm.
*Color.*—Green.
Persistence: The petals fall down when the flower is old.

Lasting quality: Long lasting on the plant, like all ivys.

THE REPRODUCTIVE ORGANS

Stamens:
*Number.*—About 7.
*Arrangement.*—Around the ovaries.
Anthers:
*Size.*—2.5 mm.
*Color.*—Light Yellow.
Filaments:
*Length.*—About 7 to 8 mm.
*Color.*—Frosted Light Yellow.
Pollen:
*Color.*—Yellow to Orange.
Pistils:
*Number.*—1 or 0.
Styles:
*Length.*—About 9 mm.
Stigmas:

*Color.*—Light Purple.
Fruit:
*Fertility.*—The fruit is fertile.
*Shape.*—Ovoid.
*Color at maturity.*—Brown.

This red purple ivy starts flowering earlier than others, maintaining its quality through spring, summer and fall. The plant remains healthy and the flowers which bloom profusely and continuously do not fade in the sun or in hot weather.

I claim:

1. The new and distinctive geranium variety, substantially as herein shown and described, characterized by its cyclamate purple flower clusters, which are borne continuously and profusely from early spring to late fall.

* * * * *

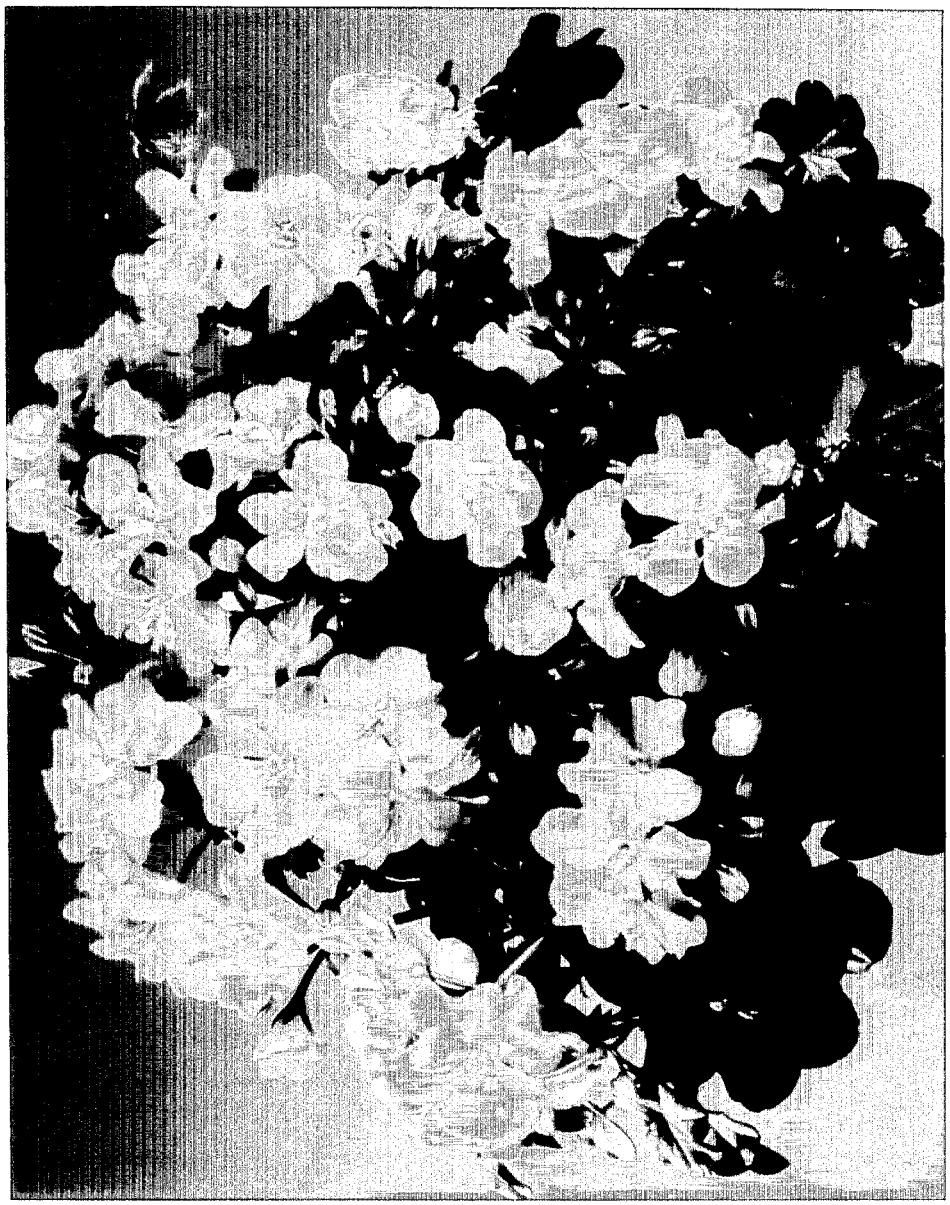

UNITED STATES PATENT AND TRADEMARK OFFICE

CERTIFICATE OF CORRECTION

PATENT NO. : Plant Patent 8,381

DATED : September 21, 1993

INVENTOR(S) : Klemm

It is certified that error appears in the above-identified patent and that said Letters Patent is hereby corrected as shown below:

Column 1, line 40, after "Growth Habit" insert --Continuously with the same quality throughout the year from early Spring through Fall.--

Signed and Sealed this

Twenty-sixth Day of July, 1994

*Attest:*

Bruce Lehman

BRUCE LEHMAN

*Attesting Officer*

*Commissioner of Patents and Trademarks*